United States Patent [19]

Mould et al.

[11] Patent Number: 5,317,378
[45] Date of Patent: May 31, 1994

[54] ENHANCING EMISSION OF EXCITED RADIATION IN AN ANALYTICAL SAMPLE SUBJECTED TO EXCITING RADIATION

[75] Inventors: Henry M. Mould; Robert Bennett, both of Buckinghamshire, England

[73] Assignee: Perkin-Elmer Ltd., Beaconsfield, England

[21] Appl. No.: 656,266

[22] Filed: Feb. 15, 1991

[30] Foreign Application Priority Data

Feb. 19, 1990 [GB] United Kingdom ............... 9003690

[51] Int. Cl.$^5$ ............... G01N 21/64; G01N 21/65
[52] U.S. Cl. ............... 356/301; 356/236; 356/318; 356/346
[58] Field of Search ........ 356/317, 318, 417, 446-448, 356/236, 301, 346; 250/228

[56] References Cited

U.S. PATENT DOCUMENTS

| | | | |
|---|---|---|---|
| 4,583,860 | 4/1986 | Butner | 356/446 |
| 4,645,340 | 2/1987 | Graham et al. | 356/301 |
| 4,684,255 | 8/1987 | Ford | 356/346 |
| 4,838,688 | 6/1989 | Rhoads | 356/336 |

FOREIGN PATENT DOCUMENTS

| | | |
|---|---|---|
| 1530546 | 11/1978 | United Kingdom . |
| 2016735A | 9/1979 | United Kingdom . |
| 1565130 | 5/1980 | United Kingdom . |
| 2044445A | 10/1980 | United Kingdom . |
| WO8606482 | 11/1986 | World Int. Prop. O. . |

OTHER PUBLICATIONS

Jarrell Ash Engineering Publications Technical Bulletin, Prepared: Jun. 1969 Preliminary EB-146, Title-Raman Spectra from the Inorganic Gases.

*Primary Examiner*—Vincent P. McGraw
*Assistant Examiner*—K. P. Hantis
*Attorney, Agent, or Firm*—Edwin T. Grimes

[57] ABSTRACT

A spherical sample cell (FIG. 4A) bears an external inwardly specular laye defining a hollow imaging mirror 11D and an optical aperture 11E. The mirror acts as an integrator of both the exciting radiation for irradiating the sample and the resulting excited radiation to be analysed, the former entering and the latter exiting through the aperture 11E. Optical integration resulting from multiple internal reflections provides multifold increase in excited radiation compared with bare cells, which is of particular advantage in Raman spectrophotometry. Alternatively, the mirror may be provided in two complementary halves in a two-part cell-holder, in which case any conventional sample cell that fits within the mirror may be used. Spectrophotometers adapted for use with the sample cell or the cell holder as well as methods based on them are described.

39 Claims, 3 Drawing Sheets

ENHANCING EMISSION OF EXCITED RADIATION IN AN ANALYTICAL SAMPLE SUBJECTED TO EXCITING RADIATION

BACKGROUND OF THE INVENTION

This invention relates to analytical-sampling devices for handling analytical samples in situations wherein liquid or vapour samples contained in said devices are to be subjected to exciting radiation at the sample station of a spectrophotometer and the resulting excited radiation (also known as stimulated radiation) is to undergo spectroscopic analysis, each device being provided with a hollow imaging mirror that in use surrounds the sample, except for an optical aperture through which the exciting radiation reaches the sample and from which the excited radiation emerges, both undergoing a large number of multiple reflections within the mirror resulting in the sensitivity of said analysis being greatly enhanced. The invention also relates to spectrophotometers co-operating with said devices and to methods of spectrophotometry based on the use of said devices.

Although the present invention may find application wherever radiation stimulated in a sample by exciting radiation is to be subjected to spectrophotometric analysis, its greatest advantage is likely to be associated with its use in laser induced fluorescence and Raman spectrophotometry; this specification will make particular reference to the latter.

It is well known in the art of Raman spectroscopy that the so called Raman effect is extremely weak and that, therefore, sophisticated sampling techniques are required to optimise the collection of the desired Raman scatter and exclude as far as possible the Rayleigh scatter. Both are the result of exciting radiation impinging upon the molecules of the samples, with the important difference, however, that in the case of the former the radiation stimulated in the sample is inelastically scattered by the molecules, and, therefore, carries with it their vibrational and rotational information that permits the Raman spectrum to be traced, whereas in that of the latter it is elastically scattered and conveys no such information but only contributes unwanted background to the Raman spectrum.

SUMMARY OF THE INVENTION

The object of the present invention is to provide analytical-sampling devices, spectrophotometers adapted to co-operate with said devices and methods of spectrophotometry based on the use of said devices, wherein the sensitivity of the spectrophotometric analysis of radiation stimulated in a sample subjected to exciting radiation may be significantly enhanced, in particular where said stimulated radiation constitutes Raman scatter.

The broad concept applied in the realization of the above object in so far as an analytical-sampling device is concerned is the provision in any such device in accordance with this invention of a hollow imaging mirror extending all around the sample except for an area occupied by an optical aperture through which the exciting radiation is made to impinge on the sample and the excited radiation is collected by the collecting optics of a spectrophotometer. The device is so constituted and arranged that by directing a narrow beam of exciting radiation through the optical aperture at a slight angle to the optical axis of the mirror, multiple reflections of the beam are produced that increase the irradiating effect of the exciting radiation upon the sample molecules. Each irradiated molecule will emit excited radiation all around, which itself will be multiply reflected by the mirror, with the result that the optical aperture of the mirror will be filled with Raman scatter enhanced by the effect of multiple reflections acting on both radiations. The effect provides what may be regarded as specular optical integration, not to be confused with the well known diffuse integration afforded by a conventional integrating sphere the inner surface of which diffuses light and cannot, therefore, be image forming.

The analytical-sampling device may be in the form of an optical sample cell embodying the hollow imaging mirror or more conveniently in the form of an optical sample-cell holder, in which case the mirror forms part of the holder and the sample is contained in a plain cell (i.e. a plain non-optical glass cell) accommodated within the holder and transparent to both radiations.

Means for locating the optical sample cell or the optical sample-cell holder at a spectrophotometric sample station and means for irradiating the sample thereat form part of a spectrophotometer or like instrument adapted in accordance with the present invention, the said spectrophotometer further including appropriate collection optics to take full advantage of the enhanced yield of excited radiation.

According to a first aspect of the present invention there is provided, as a first alternative, an analytical-sampling device in the form of an optical sample-cell including a hollow imaging mirror that in operation will surround the sample and act as an integrator for both the exciting radiation and the radiation stimulated in the molecules of the sample, the said hollow imaging mirror having an optical aperture for exiting therethrough the stimulated radiation to be submitted to spectrophotometric analysis, the area covered by the imaging surface being between 51 and 98 percent, but preferably between 80 and 97 percent, of the total area represented by the sum of the imaging surface area and the optical aperture area.

The sample retaining part of the optical sample-cell (hereinafter also optical cell) may be defined by a wall which in correspondence of the optical aperture at least is pervious to both the exciting and the stimulated radiation, the hollow imaging mirror being formed by a layer adherent to said wall which is inwardly specularly reflecting, except for an area which is left bare and represents the optical aperture of the hollow imaging mirror.

The layer may be applied to the outer surface of the optical cell wall to avoid its contamination and consequent optical degradation by the sample and in such case the wall must be pervious to both the exciting and the stimulated radiation over its entire area. However, in cases where the contamination is slight and any light scatter by the wall is undesirable, the optical cell may be internally coated with a specular layer and, consequently, the wall need only be pervious in the optical aperture area. Where the layer is external, the unwanted light scatter may be reduced to an acceptable minimum by making the wall as thin as practicable without rendering the cell too fragile for normal use. A thickness of about .2 mm is typical.

In order that the proper operative orientation of the optical aperture in relation to the optical system of the spectrophotometer by which the stimulated radiation is to be analysed may be mechanically repeated, at least approximately, thus facilitating the analyst's task of seeking it by trial and error, the optical cell may be provided with optical cell registration means, e.g. a suitably shaped flag-like projection, that when the cell is in situ at the sample station of the spectrophotometer will engage optical sample-cell locating means predeterminedly positioned thereat with respect to the said optical system, as shall presently be described in greater detail in dealing with the second aspect of the present invention.

Optical sample-cells of spherical configuration, in which the hollow imaging mirror is, therefore, spherical, are preferred but other imaging-mirror configurations suitable for the purpose of optical integration may be used.

According to a first aspect of the present invention there is provided, as a second alternative, an analytical-sampling device in the form of an optical holder for a sample cell (hereinafter optical cell-holder) including two relatively displaceable co-operating members each provided with a complementary part of a hollow imaging mirror that in operation will surround the sample in a sample cell and act as an integrator for both the exciting radiation and the radiation stimulated in the molecules of the sample, which members are adapted to be urged in use from an idle position wherein said complementary mirrors parts are supported in spaced relation for interposing the sample cell therebetween to a working position wherein the complementary mirror parts are in abutment and define said hollow imaging mirror with the sample cell located therein, the said hollow imaging mirror having an optical aperture through which the stimulated radiation will emerge in order that it may be submitted to spectrophotometric analysis.

Advantageously, each relatively displaceable member may be in the general form of a parallelepipedal slab and each complementary part of the hollow imaging mirror may actually be integral with the slab, such as by precision machining a cavity with a specular finish into its thickness around the appropriate generating axis to ensure that the rim of each complementary mirror part generated is co-planar with one of the major (i.e. extending over the larger area) surfaces of the slab.

Means may be provided for guiding the relative displacement of the slabs and ensuring that when they are brought to the working position the complementary parts of the hollow imaging mirror face each other in accurate complementary register for defining the true geometry of the hollow imaging mirror.

The slabs may include what in the idle position may be identified as integral rectilinear grooves, e.g. V-shaped grooves, one in each slab, and in the working position as a duct extending from the hollow imaging mirror, the duct being intended for accommodating therein a cell in the form of a test tube of millimetric diameter or the slender filling stem of any cell having a shape that will fit within the hollow imaging mirror.

Precision machining or optical working of each slab may be avoided if the specular surface is provided by a layer of the replicated kind, which achieves high optical performance at a low cost. Mirror replication techniques are well known. They involve depositing by vacuum evaporation a layer of aluminium upon a master which has first been coated with a molecular layer of a suitable release agent. The layer of aluminium, whilst still on the master, is bonded by an epoxy adhesive to a cavity machined to match the master approximately. The adhesive forms a bridging layer taking up any irregularities of the cavity, and when it has set the master is removed. The layer adherent to the cavity thus duplicates the accuracy of the master.

The preferred shape of the hollow imaging mirror is spherical or near spherical but as in the case of the optical sample-cells other imaging-mirror configurations suitable for optical integration may be used.

The optical cell-holder is intended for use with plain, non-optical sample-cells and offers a different balance of advantages compared to the optical sample-cell. Firstly, the handling of fragile cells is made much easier. Secondly, the positioning of the cell itself is not critical since the cell performs no optical function. Thirdly, the optical cell-holder allows the use of cells of any shape that fits within the hollow imaging mirror. Other advantages, including ease of manufacture and long life, will become apparent from the detailed description of the optical cell-holder that follows in this specification. In optical terms, it is only very slightly inferior to the alternative optical sample-cell, except that where optical imaging accuracy is taken into account, the optical cell-holder scores heavily in the ease with which it can be attained by practical manufacturing methods. At best, the difference in performance is so slight that the optical cell-holder with integral hollow imaging mirror must be regarded as the preferred embodiment of an analytical-sampling device in accordance with the present invention. In fact, in the situation where the optical sample-cell alternative is adopted, the optical cell-holder may still be used to advantage as a convenient means of handling the optical sample-cell, in which case optical cell registration means as referred to earlier may be made to engage a suitable datum of the optical cell-holder, e.g. one of the rectilinear grooves, to ensure that the optical apertures of the respective hollow imaging mirrors substantially coincide, any final adjustment that may be required being made comparatively easy as a result.

The optical sample-cell and the optical cell-holder are two alternative devices of the first aspect of the invention and give rise to two alternative spectrophotometer-cum-device adaptations or combinations in accordance with the second aspect.

According to a second aspect of the invention there is provided, as a first alternative, a spectrophotometer adapted for use with an optical sample-cell as introduced under the first aspect of the present invention, wherein the spectrophotometer comprises an optical collecting system for collecting the stimulated radiation issuing in operation from the optical aperture of the optical sample-cell and transferring it to the aperture stop of the spectrophotometer and optical sample-cell locating means for ensuring the proper location of the optical aperture relative to the collecting system.

The optical sample-cell locating means may form a structure into which the said cell may be inserted by hand and may include datum means adapted to engage the registration means of said cell, the locating means being predeterminedly fixed at the sample station of the spectrophotometer to permit the optically correct location of the optical aperture of said cell with respect to the optical collecting system.

The optical sample-cell locating means may also include means for adjusting its positioning at the sample station in the x, y and z axes.

According to a second aspect of the invention there is provided, as a second alternative, a spectrophotometer adapted for use with an optical cell-holder as introduced under the first aspect of the present invention, wherein the spectrophotometer comprises an optical collecting system for collecting the stimulated radiation issuing in operation from the optical aperture of the optical cell-holder and transferring it to the aperture stop of the spectrophotometer and optical cell-holder locating means for ensuring the proper location of the optical aperture relative to the collecting system.

The optical cell-holder locating means may form a structure into which the optical-cell holder may be slid by hand when its relatively displaceable members are abutting, the locating means being predeterminedly fixed at the sample station so as to permit in use the optically correct location of the optical aperture of said holder with respect to the optical collecting system.

Alternatively, the optical cell-holder itself may be modified so as to form part of the spectrophotometer, in which case the displaceable member in which the optical aperture is provided is predeterminedly fixed at the sample station of the spectrophotometer so that the optical aperture of said holder is at the optically correct location with respect to the optical collecting system and the said member inherently includes the optical cell-holder locating means.

In both alternatives of the spectrophotometer a laser and co-operating light deflecting means may be incorporated which are adapted to direct a beam of exciting radiation through the central region of the optical aperture in such orientation as to permit a large plurality of internal reflections to be set up within the hollow imaging mirror.

Means may be provided for adjusting the power of the laser and separate means for adjusting the cross-section of the laser beam.

Filter means may also be provided, at a convenient location in the optical system of the spectrophotometer, for attenuating unwanted radiation scatter and maximise the desired stimulated radiation.

In order to permit a desired region within the hollow imaging mirror, inaccessible through the optical aperture, to be imaged onto the aperture stop of the spectrophotometer, thus treating the region as the effective source of stimulated radiation, and effect the imaging with the desired optical matching, the collective system itself may comprise means for enabling the object an image distances to be adjusted, preferably independently.

Advantageously, the spectrophotometer may be a Raman Fourier Transform spectrophotometer.

According to a third aspect of the present invention there is provided a method of spectrophotometry of liquid or vapour samples with the aid of an optical sample-cell as introduced under the first aspect of the present invention, comprising the steps of:

a) filling the optical sample-cell with a sample;

b) irradiating the sample with a narrow beam of exciting radiation directed through the optical aperture of the hollow imaging mirror along such path as will cause the beam to undergo multiple reflections in the volume within said mirror;

c) imaging a chosen zone of higher energy density from within the hollow imaging mirror close to the optical aperture onto the aperture stop of a spectrophotometer and thus collecting the radiation stimulated in the molecules of the sample that is available at the chosen zone as a result of the multiple reflections taking place within the hollow imaging mirror and transferring it to the said aperture stop with an advantageously predetermined optical matching, the said zone thus representing the effective source of stimulated radiation, and d) analysing the stimulated radiation collected by means of a spectrophotometer.

According to a third aspect of the present invention there is additionally provided a method of spectrophotometry of liquid or vapour samples with the aid of an optical cell-holder as introduced under the first aspect of the present invention, comprising the steps of:

a) filling a suitable cell with a sample and placing it within the two parts of the hollow imaging mirror whilst the latter is in the idle position;

b) bringing the two parts of the hollow imaging mirror into close proximity;

c) with the optical cell-holder at the sample station of a suitable spectrophotometer, irradiating the sample with a narrow beam of exciting radiation directed through the central regions of the optical aperture along such path as will cause the beam to undergo multiple reflections within the volume of said mirror;

d) imaging a chosen zone of high energy density from within the hollow imaging mirror close to the optical aperture onto the aperture stop of the spectrophotometer and thus collecting the radiation stimulated in the molecules of the sample that is available at the chosen zone as a result of the multiple reflections taking place within the hollow imaging mirror and transferring it onto the said aperture stop with an advantageously predetermined optical matching, the said zone thus representing the effective source of the stimulated radiation, and e) analysing the stimulated radiation collected by means of a spectrophotometer Before the last step in each of the two methods outlined above, a filtering step may be included to attenuate the content of spurious background radiation in the stimulated radiation of interest.

The narrow beam of exciting radiation may conveniently be a laser beam, which may be focussed, collimated or divergent. The beam power is best kept in the range 1 to 500 milliwatts and the beam diameter between 1 mm and 1.5 mm. For any given volume of sample they should be chosen so that in combination they will maximise the transfer of stimulated radiation to the aperture stop of the spectrophotometer whilst avoiding loss or disintegration of sample caused by overheating thereof due to subjecting it to excessive exciting radiation energy.

The laser beam may be directed into the hollow imaging mirror through the central region of the optical aperture in such orientation as to give rise to multiple reflections of exciting radiation irradiating a vastly larger number of molecules that would be the case if, taking as an example the case of a spherical hollow imaging mirror, the beam was focussed at the centre of the sphere, when the reflected rays of exciting radiation would follow in reverse the same path as that of the incident rays and, although would contribute to the irradiation of the sample in the zone around the centre of the sphere, would in fact miss most of the molecules contained in the cell. In said example multiple reflections affecting most of the molecules in the cell are set up by slightly offsetting the beam from the path that would take it straight through the centre of the sphere. The stimulated radiation itself undergoes multiple reflections, of course. In the general case, the laser beam would be slightly offset from the or one focal point of the hollow imaging mirror.

In imaging the effective source onto the aperture stop of the spectrophotometer the optical matching may be adjusted for maximum energy transfer.

The actual location of the effective source is best sought empirically by manipulating the collecting optics used to image the said source. Adjustments of the object distance in the range 0.1 mm to 0.5 mm are significant.

Both methods are particularly suitable in FT (Fourier Transform) Raman spectroscopy, in which case the spectrophotometer referred to in both methods is an FT spectrophotometer, the aperture stop identifies with the Jacquinot stop and the stimulated radiation is Raman scatter.

To avoid as far as possible unnecessary repetition of details known from the prior art in describing embodiments of the present invention, the whole of U.S. Pat. No. 4,684,255 is imported into this specification, with the exception of the items to be identified at the beginning of the description that follows the introduction of the drawings. The said patent specification shall hereinafter be referred to as the Imported Patent.

DETAILED DESCRIPTION OF THE INVENTION

Figure 5:
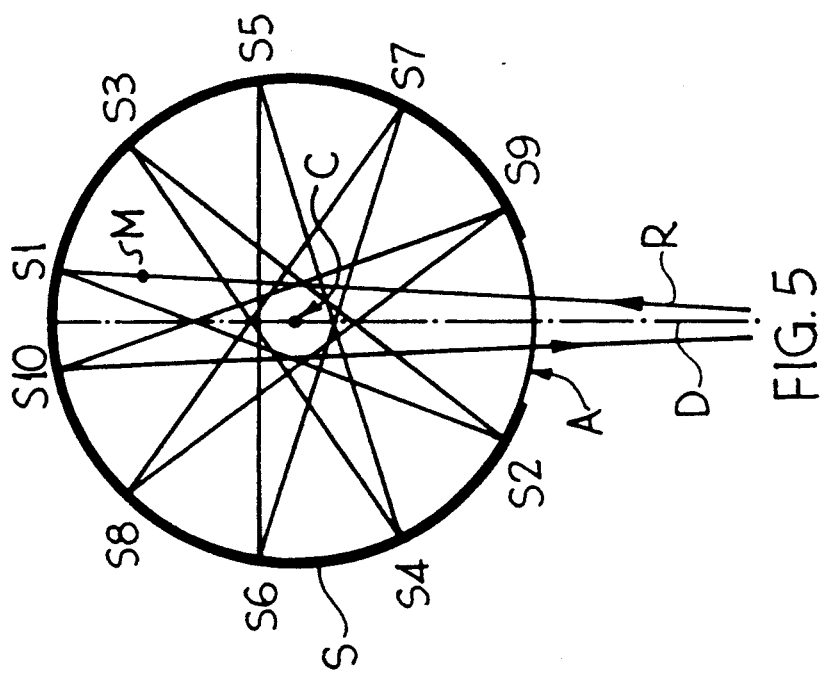
FIG. 5 is an idealized representation illustrating the optical integrating operation of the hollow imaging mirror associated with the optical cell-holder of FIG. 2 or that of FIG. 3, or the optical sample-cell of FIG. 4.

In FIG. 5 of the Imported Patent, a Fourier Transform (FT) spectrophotometer layout is shown comprising a number of optical and mechanical elements mounted on a base plate 31. In the spectrophotometer embodiment of the present invention about to be described with reference to FIG. 1 hereof, the said elements shall be regarded as forming part of a Raman FT spectrophotometer co-operating with an optical cell-holder in accordance with a first aspect of the present invention, with the exception of source 1, elliptical mirror 16 and plane mirror 18, which are found upstream of the plate 2 (FIG. 5 of the aforesaid Imported Patent) and are superseded, as presently explained.

Figure 1:
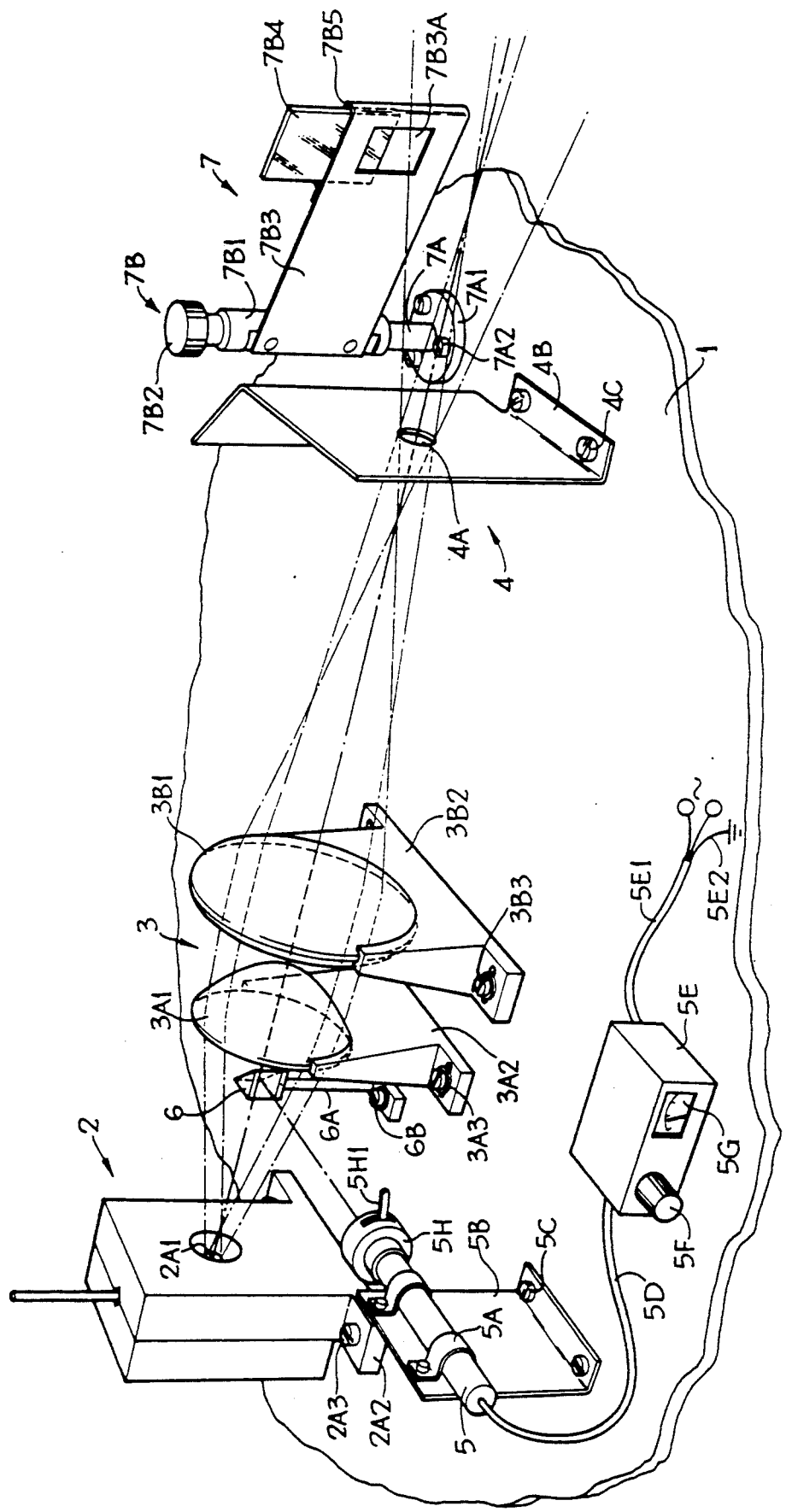
FIG. 1 illustrates a modification of the FT spectrophotometer described in the Imported Patent in combination with an optical cell-holder in accordance with a first aspect of the present invention, the said combination representing an embodiment in accordance with a second aspect of the invention.

In FIG. 1 of the present description, the only elements of FIG. 5 of the Imported Patent actually shown are the base plate 31 and the plate 2 defining the aperture stop 2A, or Jacquinot stop, of the FT spectrophotometer. The baffle plate 17, bearing aperture 17A in the form of an ellipse and integral with plate 2, is not used. It was in fact intended to co-operate with the superseded elements referred to earlier. References 2, 2A and 31 have not been retained, to avoid possible confusion between the new references and the old. Instead, plate 2 is now referenced 4; aperture 2A, 4A; and base plate 31, 1.

The base plate 1 shown in FIG. 1 supports an optical cell-holder 2 in spaced relation to a lens pair unit 3, the plate 4, a laser 5 and a right-angle prism 6, the lens pair 3 comprising aspherical lens 3A1 and biconvex lens 3B1. The supported elements defined are fastened to the base plate 1 by co-operating means, as follows: cell holder 2, by flanges 2A2 and screws 2A3; aspherical lens 3A1, by flanged mount 3A2 and screws 3A3; biconvex lens 3B1, by flanged mount 3B2 and screws 3B3; plate 4, by flange 4B and screws 4C; laser 5, by cleats 5A, flanged bracket 5B and screws 5C; and prism 6, by flanged bracket 6A and screws 6B.

The laser 5 is so positioned relative to the prism 6 acting as deflecting means, and the optical aperture 2A1 of optical cell-holder 2 that in operation the emitted laser beam will be deflected into the central region of the aperture 2A1. As will be presently explained with reference to FIG. 2, detailing the optical cell-holder 2, the laser beam so deflected serves to excite Raman scatter in a sample held in a cell accommodated within the optical cell-holder 2, with the result that the aperture 2A1 is filled with emerging Raman scatter.

For the purposes of the present description it will be assumed initially that the aperture 2A1 is nominally located at the focus of the aspheric converging lens 3A1 and any Raman scatter fanning out over a 360-degree angle around the centre of the aperture will thus be collected by the aspheric lens 3A1 and re-directed into a near parallel beam onto biconvex projection lens 3B1 separated from the plate 4 by an image distance nominally equal to the focal length of lens 3B1. Now, aperture 2A1 and aperture 4A lie on parallel planes and the centre of each lies on the optical axis of the unit 3. It follows that with the optical layout as described the aperture 4A will be imaged at the aperture 2A1 and vice versa. The object of unit 3 is, clearly, to perform the collection of the Raman scatter and its transfer to the aperture 4A with proper optical matching, so that the aperture 4A is neither unduly overfilled or underfilled with the image of the aperture 2A1 filled with Raman scatter. Unit 3 represents therefore the optical collecting system.

Where the aperture 2A1 is made conveniently smaller than the aperture 4A, the image distance of lens 3B1 will exceed the focal length by an amount appropriate to the increase in magnification ratio required for proper optical matching. In fact, the actual size of either aperture image projected at the other aperture may be readily adjusted one independently of the other since the radiation transfer between the two lenses of unit 3 is produced by a substantially parallel beam. This means that either lens may be moved slightly to adjust the size of the aperture image immediately facing it without affecting the adjustment of the other. In other words, the object and image distances may be adjusted independently. The openings in flanged mountings 3A2 and 3B2 through which screws 3A3 and 3B3 pass are elongated for the purpose of permitting the independent adjustments to be carried out after momentarily slackening the appropriate pair of fixing screws.

The laser 5 is energized through a lead 5D by the power supply 5E provided with means (not shown) for regulating the current fed to the laser 5, and hence its output power, by rotating the knob 5F. The current supplied to the laser 5 is measured by an ammeter 5G. A lead 5E1 enables the power supply 5E to be connected to a public source of AC supply, the conductor 5E2 being used to ground the housing of power supply 5E.

The output end of the laser 5 bears a generally cylindrical housing 5H within which is mounted an iris (not shown) provided with an operating lever 5H1 enabling the operator to change the cross section of the laser beam impinging upon the prism 6.

For the purpose of filtering out unwanted radiation scatter, a filter unit 7 is mounted on base plate 1 next to plate 4. Unit 7 comprises a support pillar 7A having a flange 7A1 secured to base plate 1 by screws 7A2. Rotatably mounted on the pillar 17A is an assembly 7B comprising a generally cylindrical part 7B1 terminating in a knob 7B2 and extending in a flag-like carrier 7B3 provided with an opening 7B3A, a little larger than the aperture 4A in plate 4, over which a scatter filter 7B4 may be slid in channels 7B5. By turning the knob 7B2 in the clockwise direction, the operator may swing the assembly from the position shown in FIG. 1, in which the filter is inactive, to a position where the filter is brought into close proximity with the plate 4 and is therefore active. The operator may therefore optionally interpose the filter in the optical system of the spectrophotometer or swing it out of the way.

The construction of the optical cell-holder 2 and its optical function will now be described in detail, with particular reference to FIG. 2.

Figure 2:
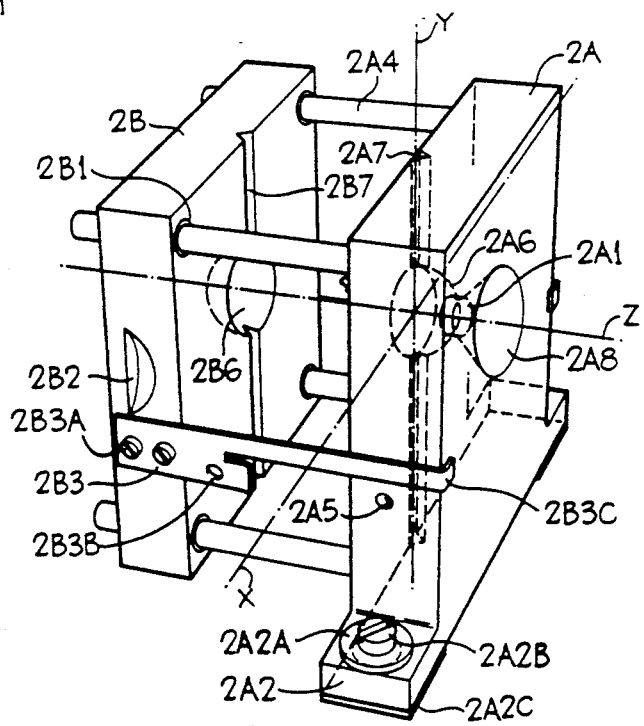
FIG. 2 is a perspective view of the optical cell-holder of FIG. 1 as an integral part of the spectrophotometer.

The optical cell-holder 2 as depicted in FIG. 2 comprises two relatively displaceable co-operating members in the form of parallelepipedal slabs of metal, 2A and 2B. Slab 2A is fixed to base plate 1 (FIG. 1) in such manner as to provide limited positional adjustment in the x, y and z axes. A washer 2A2A under screw 2A2B co-operates with an oversize hole in flange 2A2 to provide pre-set adjustment in the x and z axes. A shim 2A2C, under the flange 2A2, allows pre-set adjustment in the y axis.

It is thus clear that the flanges 2A2 in co-operation with the means described for effecting the pre-set adjustments represent optical cell-holder locating means relative to the optical collecting means. Because the construction of the optical cell-holder allows reasonably close tolerances to be maintained only a narrow range of adjustments need be provided for, mainly for the manufacturer's convenience.

The co-operating slab 2B is provided with cylindrical bearings 2B1 slidable over guide rods 2A4 solidal with slab 2A. By grasping the slab 2B between the index and the thumb of either hand at the machined depressions 2B2, the user may slide the slab 2B away from the slab 2A, to gain access to the space therebetween, or slide it towards it until the slabs abut. A sprung finger 2B3 affixed at one end to the visible side of slab 2B by screws 2B3A and free along the rest of its length to bear resiliently upon the corresponding side of slab 2A serves the dual purpose of providing a detent action for securing a firm abutment between the slabs when they are brought together and limiting the travel of slab 2B when they are separated. The first purpose is served by an inwardly facing spherical projection 2B3B co-operating with detent 2A5 in slab 2A and the second by a terminal bend in finger 2B3 forming end stop 2B3C co-operating with the front major surface of the slab 2A.

From the central region of each of the abutment faces of slabs 2A and 2B a deep hemispherical cavity, 2A6 and 2B6, extends into the slab thickness. When the slabs are brought together, after overcoming the detent action described, the hemispherical cavities define a spherical cavity that is almost complete except for the aperture 2A1, to which reference was made in describing FIG. 1. A V-shaped groove 2B7 is provided in the abutment face of 2B and a symmetrical groove 2A7, in the corresponding abutment face of slab 2A. As shown in FIG. 2, the said grooves are vertical and extend on the upper prolongations of the respective vertical diameters of the hemispheres. Their purpose is to enable a sample cell in the form of a slender transparent tube closed at the bottom end, in the manner of a test tube a few millimeters in diameter, to be accommodated therebetween when the slabs are in abutment. The grooves also serve to accommodate a slender stem of a spherical cell that may be located within the sphere defined by complementary effect of the hemispherical cavities when the slabs are brought together.

Resilient pads may be inset in slab 2B orthogonally to groove 2B7 for resiliently urging a stem against groove 2A7 when the two slabs are brought into abutment. The resilient engagement thus provided enables stems of slightly differing diameters to be properly located and held, apart from affording some positional adjustment of the sample cell along and around the vertical axis (y).

By a mirror replication technique as outlined earlier, the hemispherical cavities 2A6 and 12B6 are each provided with a specular surface and thus identify with a hollow imaging mirror part. When the slabs abut in register the parts define the hollow imaging mirror adapted to act as an optical integrator for both the exciting and the stimulated radiation. What has so far been referred to as the aperture 2A1 is in fact the optical aperture of the hollow imaging mirror. It flares out through the slab 2A into a cone 2A8 to allow for a diverging egressing beam.

It has been indicated with reference to FIG. 1 that the beam from laser 5 is directed through the central region of aperture 2A1 to excite Raman scatter in the sample within the optical cell-holder 2. It should now be added that the laser beam is directed approximately, but not exactly, along the diameter of the integrating sphere the prolongation of which passes through the centre of the aperture 2A1. As a result, the beam will undergo numerous multiple reflections while trapped within the hollow imaging mirror, which will multiply the excitation of the sample and the Raman scatter. The Rayleigh scatter is also increased, but it may be readily filtered out by means of a suitable filter, such as filter 7B4 (FIG. 1).

In addition to its improved optical functionality, to be elaborated upon presently, the optical cell-holder of FIG. 2 is quite convenient and simple in use. A sample cell may be fitted or removed by sliding the slab 2B. Assuming that slabs 2B and 2A are abutting with no cell in place and it is desired to fit a spherical cell with a long tubular stem, slab 2B is first pulled out as far as the end stop 2B3C in finger 2B3 permits, i.e. to the idle position, and then the spherical end of the cell is located in the hemispherical cavity 2A6 in slab 2A and the stem in the groove 2A7. After that the slab 2B is brought into abutment with slab 2A, i.e. at the working position, making sure that the cell is properly nested and will not be crushed. Removal of the cell is a simple matter of reversing the operation.

Figure 3A:
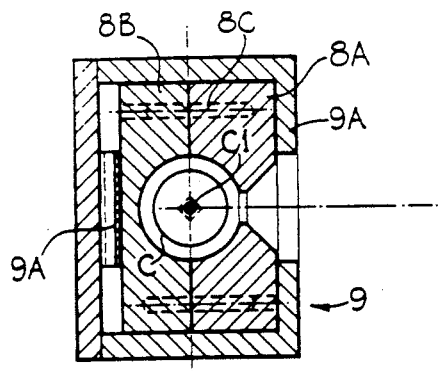
FIG. 3A is a cross-sectional plan view of FIG. 3.
Figure 3:
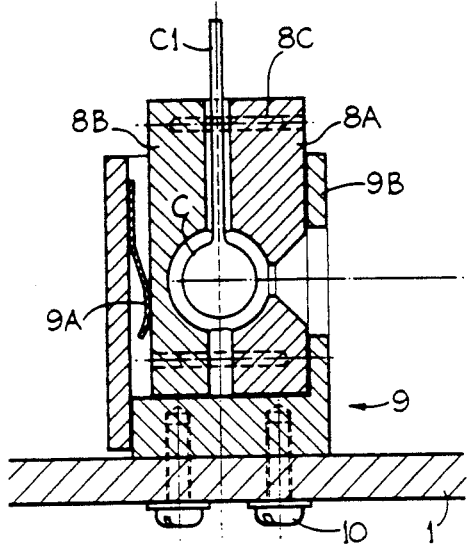
FIG. 3 is a cross-sectional side elevation of a removable optical cell-holder with co-operating housing that may be incorporated in the spectrophotometer of FIG. 1 in place of the optical cell-holder fixture of FIG. 2.

The optical cell-holder depicted in FIG. 3 and FIG. 3A is identical with that of FIG. 2 in so far as the parts performing the optical functions are concerned but it offers a different balance of convenience in handling. As shown in FIG. 3, an optical cell-holder 8 comprises slabs 8A and 8B which differ from slabs 2A and 2B of FIG. 2 only in mechanical details, in that neither has flanges for fixing to the base plate 1, neither is provided with guide rods (such as 2A4) and co-operating bearings (such as 2B1) and no stops are provided (such as finger 2B3 with end stop 2B3C) to prevent the slabs from separating completely. The slabs are kept into register by guide means in the form of dowel pins 8C but they may be readily separated when hand-held, or pressed together into abutment after a sample cell has been nested therebetween. Whilst held together in the hand under slight pressure, they may be inserted into housing 9, which is secured to the base plate 1 by screws 10 and represents optical cell-holder locating means. FIG. 3 portrays the situation after the cell holder 8, fitted with a bulbous sample cell C with long stem C1, has been inserted by the user into the housing 9, where a leaf spring 9A forces the two slabs as a unit against the wall 9B of the housing 9. The dimensions of the housing and the optical cell-holder are chosen to ensure that the optical axis of the optical cell-holder coincides with the optical axis of the lens unit 3 in FIG. 1. The housing 9 in the form of an open-top structure represents optical cell-holder locating means in predetermined spaced relation to the plate 4 (FIG. 1) defining the Jacquinot stop. Adjustability of the housing 9 in the x, y and z axes may be provided as for the optical cell-holder depicted in FIG. 2.

Figure 4:
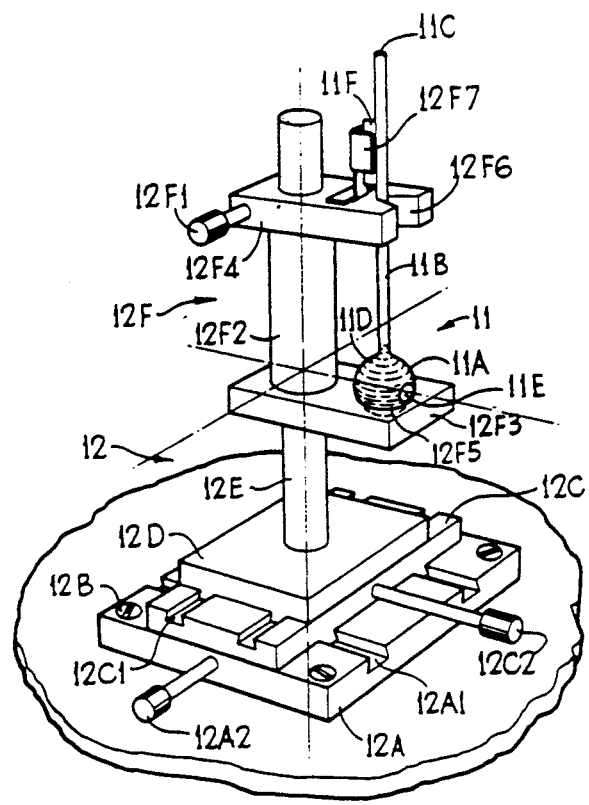
FIG. 4 is a perspective view of an optical sample-cell in accordance with a first aspect of the invention, fitted to optical sample-cell locating means.

In FIG. 4, an optical sample-cell 11 in accordance with the invention is shown fitted to optical sample-cell locating means 12 fastened to the base plate 1 in place of the fixed optical cell-holder 2 of FIG. 2.

The optical sample-cell 11 (also shown enlarged in FIG. 4A) comprises a receptacle for vapour and gas samples in the form of a bulb 11A which integrally extends into a long filling stem 11B having a small bore 11C through which a sample may be injected by means of a syringe.

Glass is preferably used in the construction of the optical sample-cell 11 because such material is cheap, easily worked and adequately inert to most samples. If the application demands it, other materials may be substituted, such as quartz.

Bulb 11A, approximately 6 mm in diameter, is externally aluminized to form an adherent coating with an inwardly reflective specular surface defining the hollow imaging mirror 11D, which in operation acts as an optical integrator. Because the coating is external, and consequently rays must pass through the wall of the bulb 11A in both directions, the wall must be pervious to both radiations. Unwanted scatter by the wall is minimized by reducing the wall thickness as far as the retention of adequate mechanical strength will allow. In the FIG. 4 embodiment, the wall thickness is about 2 mm.

The aluminized coating is continuous except for the area occupied by the root of the stem 11B and that of optical aperture 11E, about 3 mm in diameter, through which the exciting radiation is admitted and the stimulated radiation made to exit, as in the case of the optical cell-holder described earlier.

The optical sample-cell locating means 12 comprise a bottom plate 12A affixed by countersunk screws 12B to base plate 1 (see FIG. 1). Plate 12A supports two cross-slides, 12C and 12D, the first slidable on dove-tail guideways 12A1—machined into the top of plate 12A—along the z axis, under the control of a rack and pinion mechanism (not shown) operated by turning the knob 12A2, and the second slidable on dove-tail guideways 12C1—machined into the top of slide 12C—along the x axis, under the control of a second rack and pinion mechanism (not shown) operated by turning knob 12C2. The arrangement is in fact reminiscent of a conventional mechanical stage for a microscope.

Upon the slide 12D is rigidly mounted an erect pillar 12E, on which a support assembly 12F is slidable along the y axis on bearings not shown, when a rack and pinion mechanism (not shown) is brought into operation by turning the knob 12F1. In FIG. 4 the axes x, y and z are shown in dotted lines intersecting at a common point. The z axis coincides with the optical axis of the optical collecting system (see FIG. 1).

Because the rack and pinion mechanism is well known in the mechanical art, its construction has not been shown in FIG. 4, in the interest of simplification. It will suffice to say that in the case of the first named rack and pinion mechanism the rack is fixed to or machined into the underneath of the slide 12C and the pinion shaft is rotatable in bearings carried by plate 12A; in the second named mechanism, the rack is fixed to or machined into the underneath of slide 12D and the pinion shaft is rotatable in bearings carried by the slide 12C; in the third named mechanism, the rack is fixed to or machined into the pillar 12E along its length and the pinion shaft is rotatable in bearings forming part of the assembly 12F. A longitudinal channel machined into pillar 12 engages a key in assembly 12F to restrain all movements of the assembly in other than the y axis. The channel and the key are not shown.

The assembly 12F comprises a tube 12F2 integral with two horizontal ledges 12F3 and 12F4, the first being provided with a circular bore 12F5 for receiving and locating the bulb 11A and the second with a V-recess 12F6 in which the filling stem 11B locates and is retained by registration means in the form of projection 11F of the stem 11B engaging an upstanding U-spring 12F7 fastened to ledge 12F4. The rear part of ledge 12F4 additionally provides bearings (not shown) for the pinion shaft terminating at knob 12F1.

The optical sample-cell locating means 12 is intended to provide limited positional adjustment of the optical aperture 11E in the x, y and z axes, the range of slide travel indicated in FIG. 4 having been exaggerated. The arrangement of FIG. 4 is intended to assist the user in combating inaccuracies in the location of the optical aperture brought about by manufacturing imperfections. In the optical cell-holders described with reference to FIG. 2 and FIG. 3–3A, respectively, much closer tolerances may be maintained, but in any event the slab 2A (FIG. 2) and the housing 9 (FIG. 3–3A) can be accurately located at the factory and the user would not normally be expected to disturb the factory setting.

When comparing the optical cell-holder locating means such as described with reference to FIG. 2 or FIG. 3 with the optical sample-cell locating means of FIG. 4, the advantages of the optical cell-holder elaborated upon earlier in this specification become abundantly clear. It should be emphasized in particular that the accurate location of the optical aperture 11F is a necessity imposed by the comparatively wide tolerances that must be accepted when fabricating in glass or similar materials suitable for sample cell production.

Some consideration will now be given to the way the hollow imaging mirrors of the optical cell-holders of FIG. 2 and FIG. 3–3A and of the optical sample-cell of FIG. 4–4A, respectively, are able to provide a multifold increase in optical output by virtue of the optically integrating environment created around the sample for both the exciting radiation and the stimulated radiation. Because the hollow imaging mirrors in the embodiments described are optically equivalent, it will be possible to generalize in a manner applicable to all, by referring in general terms to the optical sample-cell of FIG. 4–4A, although either of the two optical cell-holders described could be referred to instead. It will be assumed for convenience of exposition, but without prejudice to the generality of the invention, that the optical output is Raman scatter which is analyzed by means of an FT spectrophotometer.

Figure 4A:
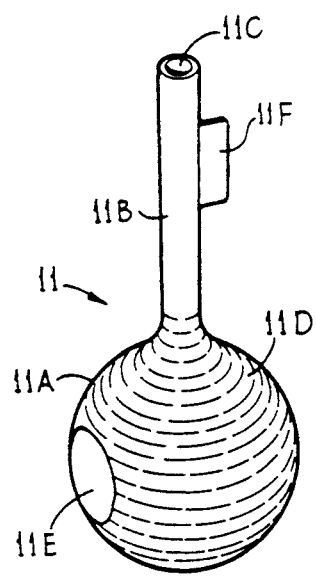
FIG. 4A is an enlarged view of the optical sample-cell of FIG. 4.

A hollow imaging mirror of spherical configuration is represented diagrammatically in FIG. 5, wherein S is a cross-section of an externally aluminized hollow sphere (such as shown in FIG. 4A), A is a circular opening in sphere S representing the optical aperture through which the exciting radiation is admitted and the stimulated radiation outputted, C is the centre of the sphere, and the dotted line D is the optical axis of the optics of the optical collecting system shown in FIG. 1.

It is evident that a narrow beam of exciting radiation entering the optical aperture A along the optical axis D, or indeed any other path passing through the centre C, would be reflected along the same path and would undergo no multiple reflections within the sphere S. If she said radiation beam is directed through the central region of the optical aperture A but slightly offset from the centre C of the sphere S, numerous internal reflections do in fact take place. A ray R from such beam is shown impinging upon the internal specular surface of the sphere S at S1 and successively reflected from S1 to S2 to S3 etc., until it emerges from the optical aperture A after being reflected from S10. Naturally, the orientation of the ray R will determine the number of internal reflections it undergoes before exiting. If the ray is only slightly offset from the centre C, the number will be greater compared with the case where it is given a considerably larger offset. The diagram of FIG. 5 can only illustrate what happens in one equatorial plane of the sphere S, but it is believed from the experimental results obtained that multiple reflections are taking place in at least a number of equatorial planes and that as a result rays such as R fan out of optical aperture A over 360 degrees around the centre thereof.

Now, if a liquid or vapour sample is contained in a sample cell within an optical cell-holder or in an optical sample-cell as described, each sample molecule such as M, receiving exciting radiation both direct and as a result of the exciting radiation having undergone multiple reflections, will emit Raman scatter photons which will also undergo multiple internal reflections and finally exit from optical aperture A. Again, the effect is three-dimensional, which means that both returning exciting radiation, of a given frequency, and the stimulated Raman radiation, of a lower frequency, will fill the optical aperture A with diverging beams directed to the collecting optics.

It has been observed experimentally that the provision of a specularly integrating environment provided by the hollow imaging mirror around the sample is capable of yielding a Raman scatter output as high as five times that obtained from the same sample without the aid of optical integration but otherwise under identical experimental conditions. It has also been observed that the energy reaching the Jacquinot stop of an FT spectrophotometer in accordance with the invention is remarkably uniform, which would seem to suggest that multiple reflections are indeed taking place in most equatorial planes of the sphere S.

Figure 6:
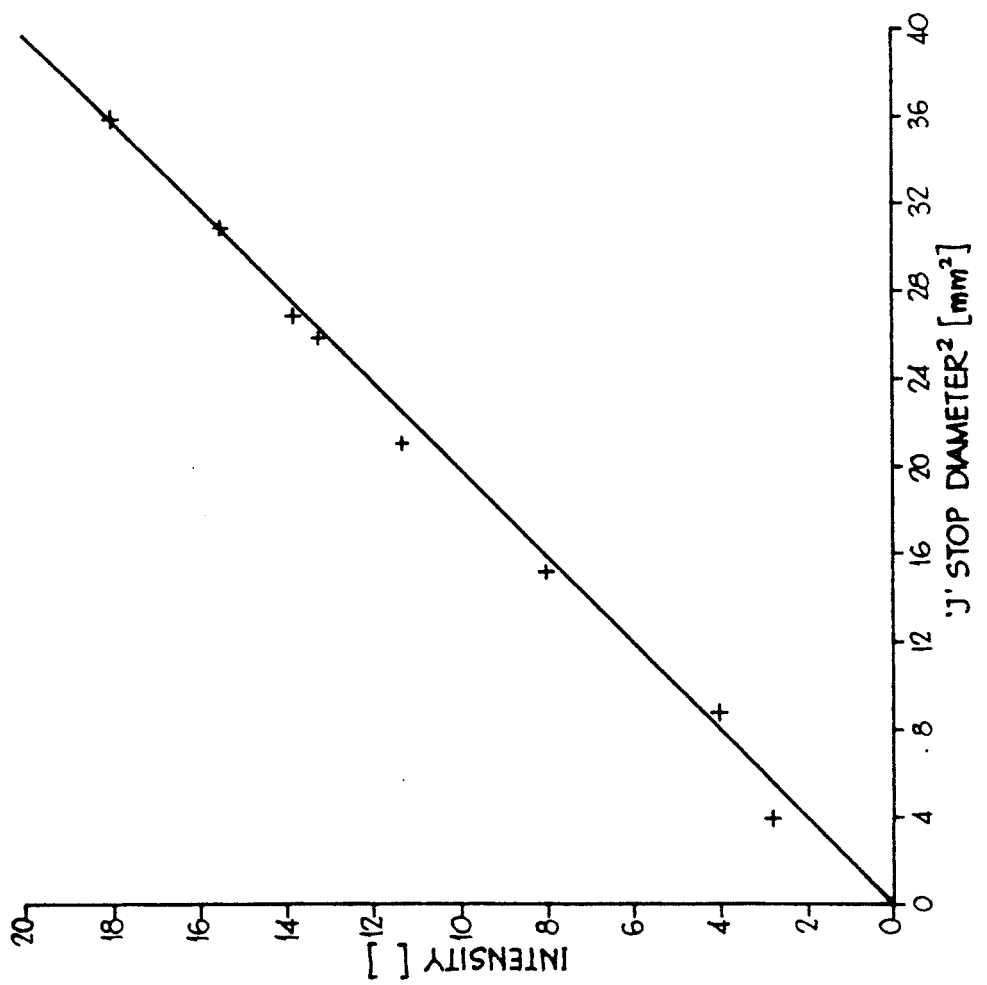
FIG. 6 is a graph plotting variations of stimulated radiation intensity at the Jacquinot stop of a Raman FT spectrophotometer, adapted to co-operate with the optical sample-cell of FIG. 4, against increases in diameter of the Jacquinot stop.

The observation was made with a Raman FT spectrophotometer adapted in accordance with the invention and an optical sample-cell of spherical configuration having a diameter of 6 mm and an optical aperture of 3 mm diameter (refer to earlier description of FIGS. 4 and 4A). Variations of the stimulated radiation intensity at the Jacquinot stop were plotted against increasing areas of the Jacquinot stop. The results are summarized in the graph of FIG. 6 which shows a linear change and thus confirms that the distribution of energy at the effective source of the stimulated radiation is substantially uniform. The departures shown in the graph do not exceed the experimental error. The laser was used in the TEM00 mode and its beam power was 250 mW. The sample in the cell was CCL4. An effective stimulated radiation source of optimum energy density was chosen.

It will be appreciated that the greater the number of internal reflections taking place within the hollow imaging mirror before a ray of exciting radiation such as R exits through the optical aperture A the greater the efficiency with which the Raman scatter is generated. This suggests that the optical aperture A should be as small as possible so as to maximize the mirror area. However, decreasing the area of the optical aperture A also means that a smaller flux of Raman scatter will be collected. In other words, a compromise must be reached between generation efficiency and collection efficiency, bearing in mind that what counts is the Raman scatter flux actually filling the Jacquinot stop of the FT spectrophotometer, the area of said stop being of course predetermined in the design of the spectrophotometer.

Experiments conducted with hollow imaging mirrors of spherical configuration have established that, given a mirror of some 6 mm in diameter having an optical aperture of some 4 mm in diameter and comparing it with a series of mirrors each of the same diameter but of gradually decreasing optical aperture diameter, the Raman scatter collected first rises to a peak and then falls. The peak denotes that an optimum compromise has been reached and the fall represents diminishing returns as the optical aperture area is reduced and the resulting increase in multiple reflections no longer provides an increase in the collected Raman scatter that overcompensates for the reduction of the area over which the scatter is collected. In the experiments referred to a peak was noted when the optical aperture diameter was reduced to around 3 mm.

A useful way of expressing the compromise is to define it in terms of the percentage that the mirror area represents of the total area given by the mirror area plus that of the optical aperture. This is a first parameter. It has been found that useful results are obtained in accordance with the invention where the hollow imaging mirror area is between 51 and 98 percent of the total area as defined, particularly good results having been achieved in the narrower range of 80 to 97 percent. As clearly shown in the schematic representation of FIG. 5, the total area as defined hereabove is substantially equal to the outer surface area of the sphere S, which represents the bulbous part of the optical sample-cell depicted structurally in FIG. 4-4A, excluding, as shown in FIG. 4-4A, the filling orifice area at the root of the stem 11B. This means that the whole of the useful surface area of the bulbous cell part is shared between the mirror and the aperture so as to achieve maximum efficiency in the quest for the compromise referred to on page 28, paragraph 1, end sentence.

The absolute value of the mirror area as distinct from the aforesaid percentage is a second important parameter because the larger the area the greater the number of internal reflections. A measure of the mirror area which applies to hollow imaging mirrors of different configurations is the volume enclosed by the mirror area. The range of volumes in which the invention is useful is between 0.08 cc and 0.4 cc, with a preferred range between 0.1 cc and 0.3 cc.

It should be observed in passing that whilst the reason for the lower volume limit is readily appreciated that for the upper limit is not so obvious. High volume is accompanied by large mirror area, which when the first parameter referred to above is accounted for may determine an optical aperture so large that its image projected by the collecting optics overfills the predetermined Jacquinot stop to such an extent as to defeat the advantage of collecting radiation from a larger area. Slight overfilling may be tolerated, however, and, depending on imponderables of design, may even be beneficial.

Having selected first and second parameters within their respective ranges, the cross-section of the exciting beam and its power may be chosen so that, having regard to the volume of the sample, excessive temperatures leading to boiling, disintegration or vaporization of the sample are avoided. Powers within the range 1 to 500 mW and laser beam diameters between 1 mm and 1.5 mm are useful in combination with the ranges given for first and second parameters.

In the context of the claims which follow, the phrases "exciting radiation" and "excited radiation" shall refer to radiation within the light spectrum that is useful for analytical purposes, such as in spectrophotometry. Furthermore, the term "sample" shall refer to a sample which allows the aforesaid radiation to be transmitted therethrough at least to an extent that renders it useful for said purposes. Typically, the present invention is applicable to many liquid and vapour samples.

What is claimed is:

1. An analytical optical sample-cell within which a fluid sample will in operation be subjected to exciting radiation at the sample station of an analytical instrument for the purpose of enabling the excited radiation emitted by the sample to be analysed, the fluid sample being pervious to both radiations, comprising:
   a) a hollow imaging mirror having an inner imaging surface which in operation surrounds the sample and acts as a specular optical integrator by virtue of the fact that the said mirror enables both radiations to be multiply reflected within the sample;
   b) a hollow bulbous fluid-sample retaining part defined by a wall having a small filling orifice, an outer surface to which the inner imaging surface of the hollow imaging mirror adheres and a substantially co-extensive inner surface adapted to enclose the sample completely except for the small filling orifice, via which the bulbous part may be filled with fluid sample by means of a syringe, the wall of the bulbous part being pervious to both radiations; and
   c) a single optical aperture in said mirror through which the exciting radiation will be admitted and the excited radiation will exit, the area of the actual imaging surface of the said mirror being between 51 and 98 percent of the total area represented by the sum of the area covered by the imaging surface and the area of the optical aperture, said sum being substantially equal to the area of said outer surface of the bulbous part, excluding the filling orifice area.

2. An optical sample-cell as claimed in claim 1, wherein the area of the imaging surface is between 80 and 97 percent of the said total area.

3. An optical sample-cell as claimed in claim 1, wherein the imaging surface of the hollow imaging mirror is the inner surface of a suitable coating on the outer surface of the wall defining the bulbous part.

4. An optical sample-cell as claimed in claim 3, wherein the coating is a thin vacuum-evaporated aluminium layer.

5. An optical sample-cell as claimed in claim 1, wherein the volume enclosed by the inner surface of the bulbous part is between 0.08 and 0.4 cc.

6. An optical sample-cell as claimed in claim 5, wherein the volume enclosed by the inner surface of the bulbous part is between 0.1 cc and 0.3 cc.

7. An optical sample-cell as claimed in claim 1, wherein the wall thickness of the hollow bulbous part is between 0.1 mm and 0.2 mm.

8. An optical sample-cell as claimed in claim 1, wherein the optical sample-cell includes registration means to facilitate the proper orientation of the optical aperture when the optical sample-cell is in situ at the sample station of an analytical instrument used to analyse the excited radiation.

9. An optical sample-cell as claimed in claim 1, wherein the imaging surface of the hollow imaging mirror is spherical and the outer surface of the wall defining the hollow bulbous part is also spherical.

10. An optical sample-cell as claimed in claim 1, wherein the wall defining the hollow bulbous part integrally extends into a slender elongated filling stem having a small bore representing the filling orifice.

11. An optical sample-cell as claimed in claim 10, wherein the filling stem is integral with registration means which when engaged by co-operating means provided at the sample station of an analytical instrument will enable the single optical aperture to be properly orientated relatively to the optical means provided in said instrument for the collection of the excited radiation.

12. An optical sample-cell as claimed in claim 11, wherein the registration means is in the form of a projection extending radially from the filling stem.

13. A spectrophotometer which in operation co-operates with an analytical optical sample-cell as claimed in claim 1, comprising:
   a) a spectrophotometer having an aperture stop and an optical collecting system for collecting the excited radiation issuing in operation from the optical aperture of the optical sample-cell and transferring it to the aperture stop of the spectrophotometer;

b) optical sample-cell locating means to ensure the proper location of the optical aperture of the optical sample-cell relative to the optical collecting means; and c) a laser and co-operating light deflecting means adapted to direct a beam of exciting radiation through the central region of said optical aperture in such orientation as to permit a large plurality of internal reflections to be set up within the hollow imaging mirror of the optical sample-cell.

14. A spectrophotometer as claimed in claim 13, wherein the locating means enables the positioning of the optical aperture to be adjusted independently in the three orthogonal x,y, and z axes.

15. A spectrophotometer as claimed in claim 13, wherein the optical sample-cell as claimed in claim 1 further includes registration means which in operation is engaged by the optical sample-cell locating means, whereby to ensure repeatability of the proper operative orientation of the sample-cell aperture.

16. An optical holder for a plain analytical sample-cell in which there are distinguished a first sample-retaining cell portion, within which a fluid sample will in operation be subjected to exciting radiation at the sample station of an analytical instrument for the purpose of enabling the excited radiation emitted by the sample to be analysed, and a second cell portion for filling and handling the cell, said second portion longitudinally extending from the first cell portion, the first cell portion and the sample being transparent to both radiations, said optical holder comprising:

a) two relatively displaceable co-operating members which in operation are eased apart by the user for interposing a filled sample cell as aforesaid therebetween and then are gently pressed together for nesting the sample cell therebetween;

b) a complementary part of a hollow imaging mirror in each member within which part a first cell portion as aforesaid will be nested as the members are pressed together;

c) a single optical aperture in one of the two complementary parts, through which the exciting radiation will be admitted and the excited radiation will exit;

d) a complementary part in each member of sample cell positioning means that will engage a second sample-cell portion as aforesaid as the members are pressed together; and e) co-operating registration means in each member ensuring that when the members are brought into close abutment with the sample cell nested therebetween the two complementary mirror parts define a complete hollow imaging mirror acting as a specular integrator by virtue of the fact that the said mirror enables in operation both radiations to be multiply reflected within it and hence within the sample and the complementary sample cell positioning parts define a complete sample-cell positioning means which engages the second sample cell portion and locates the first sample cell portion within the hollow imaging mirror.

17. An optical holder for a plain analytical sample-cell as claimed in claim 16, wherein each relatively displaceable member is in the general form of a parallelepipedal slab having an abutment face for providing a close abutment between the members and the associated complementary part of the hollow imaging mirror is a specular surface in a cavity of the member.

18. An optical holder for a plain analytical sample-cell as claimed in claim 17, wherein the cavity in each slab extends so as to extend from a region of the abutment face of the slab into the thickness of the slab.

19. An optical holder for a plain analytical sample-cell as claimed in claim 18, wherein the specular surface is a replicated-from-master surface in a layer adherent to the surface of the cavity.

20. An optical holder for a plain analytical sample-cell as claimed in claim 19, wherein each complementary part of the sample cell positioning means is a rectilinear groove provided in each slab extending from the cavity, and the complete sample-cell positioning means is a channel, that will be formed by the co-operation between the grooves as the displaceable members are brought into abutment.

21. An optical holder for a plain analytical sample-cell as claimed in claim 16, wherein the volume enclosed by the hollow imaging mirror is between 0.08 cc and 0.4 cc.

22. An optical holder for a plain analytical sample-cell as claimed in claim 16, wherein the volume enclosed by the hollow imaging mirror is between 0.1 and 0.3 cc.

23. An optical holder for a plain analytical sample-cell as claimed in claim 16, wherein the hollow imaging mirror is spherical.

24. A spectrophotomer which in operation co-operates with an optical holder for a plain analytical sample-cell as claimed in claim 16, comprising:

a) a spectrophotometer having an aperture stop and an optical collecting system for collecting the excited radiation issuing in operation from the optical aperture of an optical holder as aforesaid and transferring it to the aperture stop of the spectrophotometer;

b) locating means for ensuring the proper location of the optical-holder single optical aperture relative to the optical collecting system; and c) a laser co-operating with light deflecting means to direct a laser beam of exciting radiation through the central region of said optical aperture in such orientation as to permit a large plurality of internal reflections to be set up within the hollow imaging mirror of the optical holder.

25. A spectrophotometer as claimed in claim 24, wherein the optical holder is integral with a co-operating spectrophotometer by virtue of the fact that the displaceable member including the optical aperture is predeterminedly fixed relatively to the optical collecting system and thus inherently includes the said locating means.

26. A spectrophotometer as claimed in claim 24, wherein the locating means is in the form of a structure into which the co-operating members of optical holder may be slid in abutment and retained therein with the optical aperture in a predetermined optically correct location with respect to the optical collecting system.

27. A spectrophotometer as claimed in claim 24, comprising means for adjusting the power of the laser beam and means for adjusting the cross-section of the laser beam.

28. A spectrophotometer as claimed in claim 24, comprising a filter for attenuating unwanted excited radiation and maximising desired excited radiation, the filter being located in close proximity to the aperture stop of the spectrophotometer.

29. A spectrophotometer as claimed in claim 24, wherein the spectrophotometer is a Raman Fourier Transform spectrophotometer and the aperture stop of the spectrophotometer is the Jacquinot stop.

30. As spectrophotometer as claimed in claim 24, wherein the optical collecting system includes means for adjusting the optical matching between the effective source of the excited radiation and the aperture stop of the spectrophotometer by permitting the image and object distances to be independently adjusted.

31. A spectrophotometer as claimed in claim 24, wherein the optical collecting system includes means for selecting as the effective source the region within the hollow imaging mirror accessed through the optical aperture where the concentration of excited radiation is more advantageous.

32. A method of spectrophotometry comprising the steps of:
 a) injecting a fluid sample in an analytical optical sample-cell comprising a hollow imaging mirror having an inner imaging surface surrounding the sample and thus acting as a specular optical integrator, except for an area not significantly larger than that occupied by an optical aperture, by virtue of the fact that the said mirror enables, in the performance of this method, both exciting radiation impinging upon the sample and excited radiation emitted by the sample to be multiply reflected within the sample;
 b) locating the analytical optical sample-cell at the sample station of a suitable spectrophotometer having an aperture stop;
 c) irradiating the sample with a narrow beam of exciting radiation directed through the optical aperture of the hollow imaging mirror along such path as will cause the beam to undergo multiple reflections in the volume within said mirror;
 d) imaging a chosen zone of near optimum energy density from within the hollow imaging mirror close to the optical aperture onto the aperture stop of said suitable spectrophotometer and thus collecting the radiation excited in the molecules of the sample that is available at the chosen zone as a result of the multiple reflections taking place within the hollow imaging mirror and transferring it to said aperture stop with an advantageously predetermined optical matching, the said zone thus representing the effective source of excited radiation; and
 e) analysing by means of said suitable spectrophotometer the excited radiation collected.

33. A method as claimed in claim 32, wherein the narrow beam of exciting radiation is a laser beam.

34. A method as claimed in claim 33, wherein the power and the cross-section of the laser beam are adjusted in relation to the sample volume so that excessive temperatures leading to loss or disintegration of the sample are avoided.

35. A method as claimed in claim 32, wherein the method is a method of Raman Fourier Transform spectrophotometry and the spectrophotometer is a Raman Fourier Transform spectrophotometer.

36. A method of spectrophotometry comprising the steps of:
 a) filling a plain analytical sample-cell with a fluid sample to be analysed;
 b) placing the plain analytical sample-cell between relatively displaceable co-operating members of an optical holder for said cell, each member comprising a complementary part of a hollow imaging mirror provided with an optical aperture in one of the parts;
 c) urging the said parts to abut with the plain analytical sample-cell nesting within the hollow imaging mirror;
 d) locating the optical holder at the sample station of a suitable spectrophotometer having an aperture stop;
 e) irradiating the sample with a narrow beam of exciting radiation directed through the central region of the optical aperture along such path as will cause the beam to undergo multiple reflections within the volume of said hollow imaging mirror;
 f) imaging a zone of near optimum high energy density from within the hollow imaging mirror close to the optical aperture onto the aperture stop of said suitable spectrophotometer and thus collecting the radiation excited from the molecules of the sample that is available at the chosen zone as a result of the multiple reflections taking place within the hollow imaging mirror and transferring it onto said aperture stop with an advantageously predetermined optical matching, the said zone thus representing the effective source of stimulated radiation; and
 g) analysing by means of the spectrophotometer the excited radiation collected.

37. A method as claimed in claim 36, wherein the narrow beam of exciting radiation is a laser beam.

38. A method as claimed in claim 37 wherein the power and the cross-section of the laser beam are adjusted in relation to the sample volume so that excessive temperatures leading to loss or disintegration of the sample are avoided.

39. A method as claimed in claim 36, wherein the method is a method of Raman Fourier Transform spectrophotometry and the spectrophotometer is a Raman Fourier Transform spectrophotometer.

* * * * *